(12) United States Patent
Brady et al.

(10) Patent No.: US 6,359,177 B1
(45) Date of Patent: Mar. 19, 2002

(54) PROCESS FOR SEPARATING MIXTURES OF MATERIALS HAVING DIFFERENT BOILING POINTS

(75) Inventors: Bill L. Brady, Duesseldorf; Guenther Weymans, Kuerten-Bechen, both of (DE); Berthold Keggenhoff, Houston, TX (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/738,297

(22) Filed: Dec. 15, 2000

(51) Int. Cl.[7] ............................................. C07C 209/00
(52) U.S. Cl. ..................... 564/424; 564/437; 422/193; 422/194; 422/195; 422/234
(58) Field of Search ................... 564/424, 437; 422/193, 194, 195, 234

(56) References Cited

U.S. PATENT DOCUMENTS

| | | | |
|---|---|---|---|
| 4,480,129 A | 10/1984 | Priegnitz et al. | 564/424 |
| 5,684,180 A | 11/1997 | Knöfel et al. | 560/347 |
| 5,728,880 A | 3/1998 | Beckhaus et al. | 564/305 |

*Primary Examiner*—Samuel Barts
(74) *Attorney, Agent, or Firm*—Joseph C. Gil; Lyndanne M. Whalen

(57) ABSTRACT

A mixture of materials having different boiling points is separated into fractions having different boiling points. The separated fraction containing the desired product is stripped using the vapors of a lower boiling fraction. The process of the present invention is particularly useful for recovering a desired isomer or isomer mixture from a technical mixture obtained during production of an aromatic amine such as toluenediamine. Little or no unwanted isomer or by-product is present in the isomer or isomer mixture product of this process.

9 Claims, 4 Drawing Sheets

PROCESS FOR SEPARATING MIXTURES OF MATERIALS HAVING DIFFERENT BOILING POINTS

BACKGROUND OF THE INVENTION

The present invention relates to a process for separating mixtures of materials having different boiling points. More particularly, it is a process for separating a technical product containing both a desired product and unwanted byproducts. This process is particularly effective for separating isomers, especially isomeric mixtures of amines.

Many production processes yield mixtures of materials containing high boiling residues and low-boiling isomers that need to be separated in order to recover the desired product. One example of such a process is the process for producing aromatic amines such as toluene diamine ("TDA"). Processes for the production of aromatic amines are known. One such process is disclosed in U.S. Pat. No. 5,728,880. In the known processes for the production of aromatic amines, the hydrogenation product is generally an isomeric mixture of amines from which the desired isomer or mixture of isomers needs to be separated.

Several techniques for achieving such separation are known. In the technique disclosed in U.S. Pat. No. 5,728,880, for example, any solvent present or water generated by the hydrogenation reaction is removed from the reaction mixture. The resultant mixture is then distilled to separate the low boiling amine isomers from the high boiling by-product materials present. The high boiling by-product materials and some of the meta-isomer remaining in the distillation residue are then concentrated and mixed with some of the ortho-isomer. This mixture is then distilled to remove the meta- and ortho-isomers which are subsequently returned to the TDA isomer distillation column. One advantage of this patented technique is the relatively low amount of additional energy input needed to separate the high boiling component(s). However, the amount of m-TDA recovered is less than optimum. To optimize recovery of the meta isomer, excessive amounts of the ortho isomer must be used. However, use of such large amounts of the ortho isomer causes a high load on the TDA isomer distillation column.

U.S. Pat. No. 5,684,180 also discloses a process for the separation and purification of aromatic polyamine mixtures. In the process described in U.S. Pat. No. 5,684,180, the polyamine-containing reaction mixture is mixed with a two-phase system in a first extraction stage that operates on a counter-current principle. Multi-stage distillation is subsequently used to further separate the components of the polyamine mixture. This patented process is commercially undesirable because it requires a high amount of energy and a costly distillation unit to separate the amine product from the extraction medium.

U.S. Pat. No. 4,480,129 discloses another process for separating isomers, specifically isomers of toluidine. In this disclosed process, the isomer mixture is contacted with an adsorbent satisfying specified compositional requirements to selectively adsorb the p-toluidine. This patented process would not be useful for separating mixtures of materials other than toluidine because high boiling by-products would be expected to foul the adsorbent taught to be necessary to achieve the desired separation. Handling of the solids generated in the course of this process makes commercial use of the process difficult.

SUMMARY OF THE INVENTION

It is an object of the present invention to provide a process and an apparatus useful for separating mixtures of materials having different boiling points.

It is also an object of the present invention to provide a process and apparatus useful for separating mixtures of amines, particularly mixtures containing different isomers of an amine, which process and apparatus do not require as much expensive equipment and energy as the known prior art processes and apparatus.

It is another object of the present invention to provide a process and apparatus useful for separating mixtures, particularly isomer mixtures of amines, in which the amount of the desired isomer(s) recovered is significantly greater than the amounts generally recovered by known prior art separation processes and apparatus.

It is a further object of the present invention to provide a process and apparatus useful for separating a desired amine isomer or isomer mixture from an isomeric mixture in which the amount of the desired isomer lost is substantially less than that lost in prior art processes and apparatus.

It is an additional object of the present invention to provide a flexible process and apparatus for separating amine mixtures.

These and other objects which will be apparent to those skilled in the art are accomplished by treating a mixture of materials having different boiling points to separate that mixture into fractions having different boiling points. The fraction containing the desired product is fed to a stripping column in which it is stripped using the vapors of a lower boiling fraction. The desired isomer or isomer mixture in which little or no unwanted isomer or by-products are present is recovered.

DETAILED DESCRIPTION OF THE INVENTION

Figure 1:
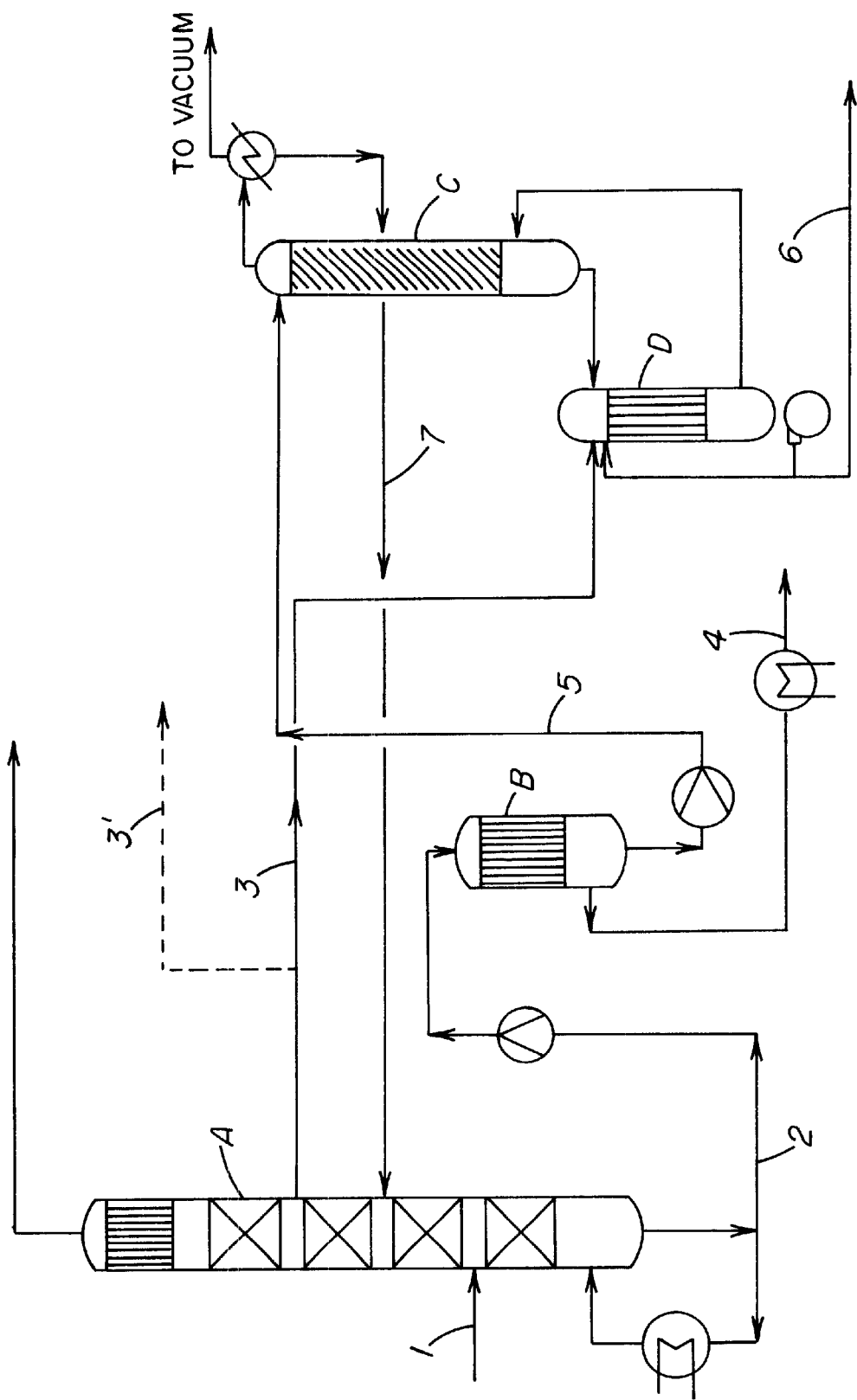
FIG. 1 illustrates an apparatus suitable for carrying out the separation of a mixture in accordance with one embodiment of the process of the present invention. In this illustrated embodiment, the starting mixture is separated into a low boiling fraction and a sump product. The sump product is subsequently treated to recover the desired product.

The present invention relates to a process and apparatus useful for separating a mixture of materials having different boiling points, particularly to a process for stripping low boiling isomers (e.g., isomers of aromatic amines) from a mixture containing higher boiling materials. In a particularly preferred embodiment of this process, low boiling isomers of toluene diamine are separated from a technical mixture generated in the course of producing toluene diamine from dinitrotoluene.

As used herein, the terms "high boiling", "intermediate boiling" and "low boiling" are relative with respect to the particular mixture to be separated rather than to a specific temperature range. That is, the "high boiling" fraction of a given mixture is that fraction which has the highest boiling point of any fraction separated from that mixture. The "low boiling" fraction is that fraction which has the lowest boiling point of any fraction separated from that mixture. The "intermediate boiling" fraction(s) of a given mixture has/have a boiling between that of the highest boiling and lowest boiling fractions.

As used herein, the "relative vapor pressure" of one fraction of the mixture to be separated to a second fraction of the same mixture is the ratio of the vapor pressure of the first fraction to the vapor pressure of the second fraction.

For the process of the present invention to be effective, the relative vapor pressure of the intermediate boiling fraction to the high boiling fraction should be at least 3:1, preferably at least 25:1. The relative vapor pressure of the low boiling fraction to the intermediate boiling fraction should be at most 30:1, preferably no greater than 5:1.

In a preferred embodiment of the process of the present invention, the mixture containing the material to be separated ("starting mixture") is separated into a low boiling fraction which is recovered in the vapor phase and a high boiling fraction. The high boiling fraction is generally recovered as a residue. The relative volatility of the low boiling fraction to the higher boiling fraction should be at least 3:1, preferably 25:1 or higher. This higher boiling fraction recovered as residue in the first separation is further treated to separate at least one intermediate boiling fraction from that residue. In this second treatment, the intermediate boiling fraction is recovered as the vapor phase and the high boiling fraction is recovered as the bottoms product. In this second bottoms product, the relative amount of high boiling material(s) present has been substantially increased. This second bottoms product is then treated, e.g., in a stripping column in which vapors of the low boiling fraction generated in the first separation step are used as the stripping agent. An intermediate fraction composed of high boiling and low boiling materials in which the relative amount of low boiling material is higher than in the fraction recovered as the bottoms product of the second separation is recovered as a distillate from the stripping column and recycled to the initial separation stage of the process of the present invention.

The process of the present invention can, in principle, be used to separate any mixture of materials having sufficiently different boiling points to enable separation by distillation. This process is, however, particularly useful for separating mixtures of amines, most preferably isomeric mixtures of amines such as toluene diamine.

The toluene diamine ("TDA") mixtures preferably used as the starting material in the practice of the present invention may be obtained from any of the known processes for producing aromatic amines. Such mixtures generally include the ortho- and meta-isomers of TDA, high boiling by-products, any solvent present during the reaction, and water generated during the reaction.

In the practice of the present invention, it is preferred but not necessary that any organic solvent and water of reaction be removed from the amine mixture prior to separation of the mixture into fractions. The starting mixture from which product is to be recovered may be separated, e.g., by distillation, into the desired number of fractions. Typically three fractions are generated during the process of the present invention but more than three fractions may be generated to achieve process efficiencies, purer products or a greater variety of isomer mixtures.

Any of the known techniques and commercially available equipment may be used to carry out separation of a starting mixture in accordance with the present invention. The technique which is most typically used, is distillation. Distillation equipment with multiple stage columns is particularly preferred. Examples of suitable distillation equipment include columns with trays (either sieve or valve trays) and packed columns (structured or random packing).

Where the starting mixture has been generated by hydrogenating dinitrotoluene, the starting mixture will typically contain less than 5% by weight of ortho-isomers of TDA, less than 5% by weight residue and the remainder of the mixture will be the meta-isomers of TDA. In the preferred embodiment of the process of the present invention, the low boiling fraction recovered from the first separation stage would typically include less than 5% by weight of the meta-isomers of TDA and at least 95% by weight of the ortho-isomers of TDA. The sump or bottoms product of the first separation stage would typically contain less than 1% by weight of the ortho-isomers of TDA, less than 5% by weight of the by-products with the remainder being the meta-isomers of TDA. The sump product of the first separation stage of the process of the present invention is then subjected to a second separation. In this second separation stage, the top product (i.e., distillate or vapor phase product) recovered is meta-TDA isomers with less than 1% by weight ortho-TDA. The sump of the second separation stage will typically contain from 10–70% by weight of high boiling by-products, less than 1% by weight ortho-isomers of TDA, and the remainder will be meta-isomers of TDA.

After the starting mixture has been separated into fractions, the high boiling fraction recovered, e.g., as a distillation residue, from the second separation stage may be introduced into a stripping column where that fraction is stripped using all or a portion of the low boiling fraction (i.e., the o-TDA-containing fraction) in its vapor phase. The bottoms product recovered from this stripping column is typically a mixture of low boiling and high boiling materials which mixture has an intermediate boiling point. The distillate recovered from the stripping column is a mixture of the low boiling ortho-TDA and meta-TDA in which the lower boiling ortho-TDA is present in a greater amount. This distillate mixture of o-TDA and m-TDA is recycled to the initial separation stage in which separation of the starting mixture is conducted.

The number of stages in the stripping column used to strip the high boiling fraction with the low boiling fraction may have a direct effect upon the amount of desired product remaining in the final residue. It has been found that as the number of stripping stages increased, the m-TDA content in the final bottoms product decreased.

Any of the commercially available stripping columns may be used in the practice of present invention. It is preferred, however, that the stripping column have at least 3 stages, preferably at least 5 stages, most preferably from 5 to 30 stages. Examples of commercially available stripping columns useful in the practice of the present invention include columns having trays (sieve or valve trays) and packed columns (random, structured or grid packing).

The stripping column is generally operated at a temperature of from about 116 to about 260° C., preferably from about 120 to about 250° C., when the mixture to be separated is an isomer mixture of toluene diamine.

The bottoms product recovered from the stripping column will generally include from about 10 to about 80% by weight (based on total weight of bottoms product) of high boiling by-products, preferably from about 30 to about 70% by weight. The remainder of the bottoms product is composed of o-TDA and less than 4% by weight, preferably less than 2% by weight m-TDA.

The distillate recovered from the stripping column will generally include from about 55 to about 98% by weight (based on total weight of distillate), preferably from about 78 to about 96% by weight of o-TDA. The remainder of the distillate is m-TDA.

The process of the present invention will be further described in greater detail with reference to FIGS. 1–4.

In the apparatus illustrated in FIG. 1, the starting mixture shown as stream 1 is fed to separation column A in which that starting mixture is separated into stream 2 and stream 3. Stream 2 is substantially composed of m-TDA and is recovered from column A as a bottoms product. Stream 3 is substantially composed of o-TDA and is recovered as the top product or distillate from column A.

Stream 2 which is substantially composed of m-TDA is fed to evaporator B where it is separated into streams 4 and 5. Stream 4, the distillate recovered from evaporator B, is composed of m-TDA in which minor amounts of o-TDA may be present. Stream 4 represents the desired product which is to be recovered by the process of the present invention. Stream 5 is the sump product stream of evaporator B and is fed to stripping column C.

Stream 3 is substantially composed of o-TDA. All or a portion of stream 3 is fed to evaporator D of stripping column C. The bottoms stream 6 composed of o-TDA and high boiling materials is recovered. If only a portion of stream 3 is fed to evaporator D, the remaining portion of that stream 3 (represented in FIG. 1 by a dotted line) may be recovered.

Stream 7 recovered as the distillate from stripper column C and in which o-TDA is present in a significantly greater amount than m-TDA is fed to separation column A.

Figure 2:
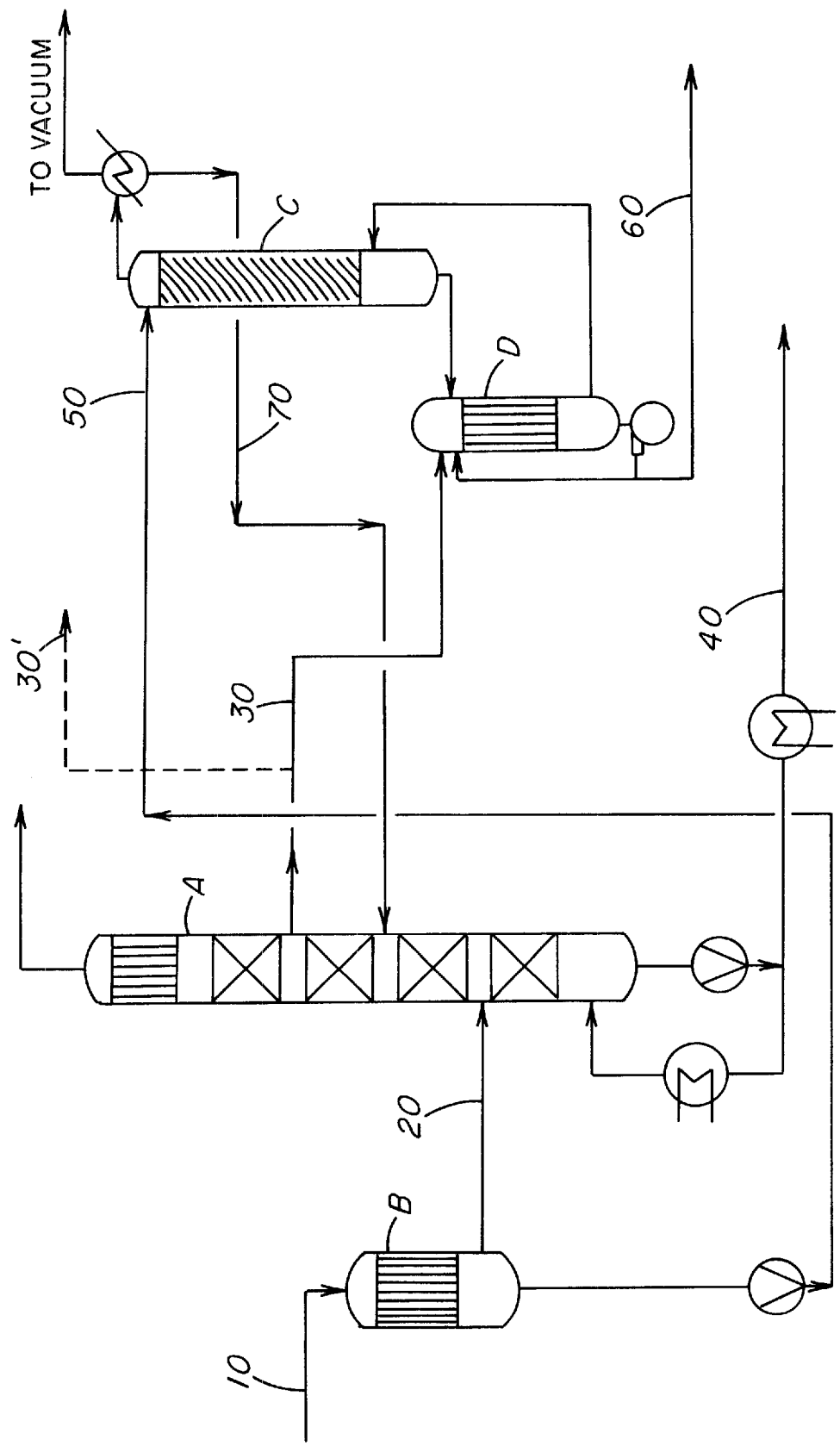
FIG. 2 illustrates an apparatus suitable for carrying out the separation of a mixture in accordance with a second embodiment of the process of the present invention. In this illustrated embodiment, the starting mixture is separated into a mixture containing the desired product and a sump product which contains unwanted high-boiling by-products. The sump product is subsequently treated to recover the desired products from the unwanted low-boiling by-products.

In the apparatus shown in FIG. 2, the starting mixture is shown as stream 10. Stream 10 is fed to evaporator column B in which it is separated into streams 20 and 50. Stream 20 which is substantially composed of m-TDA in which up to 5% ortho-TDA may be present, is fed to separation column A in which stream 20 is separated into stream 30 which is substantially composed of ortho-TDA and stream 40 which is substantially composed of meta-TDA, the desired product. Where only a portion of stream 30 is to be used in subsequent separation steps, the portion of stream 30 which is removed from the process is represented by a dotted line in FIG. 2.

All or a portion of stream 30 which is recovered as the top product is then fed to evaporator D of stripping column C in which it is vaporized prior to being fed to stripping column C. Stream 60 composed substantially of ortho-TDA and high boilers is recovered from evaporator D.

Stream 50 which is substantially composed of meta-TDA and high boiling material is recovered as a bottoms product from evaporator column B is fed to stripper column C.

Stream 70 composed substantially of ortho-TDA and meta-TDA is recovered from stripper column C as a distillate and is fed to separation column A.

Figure 3:
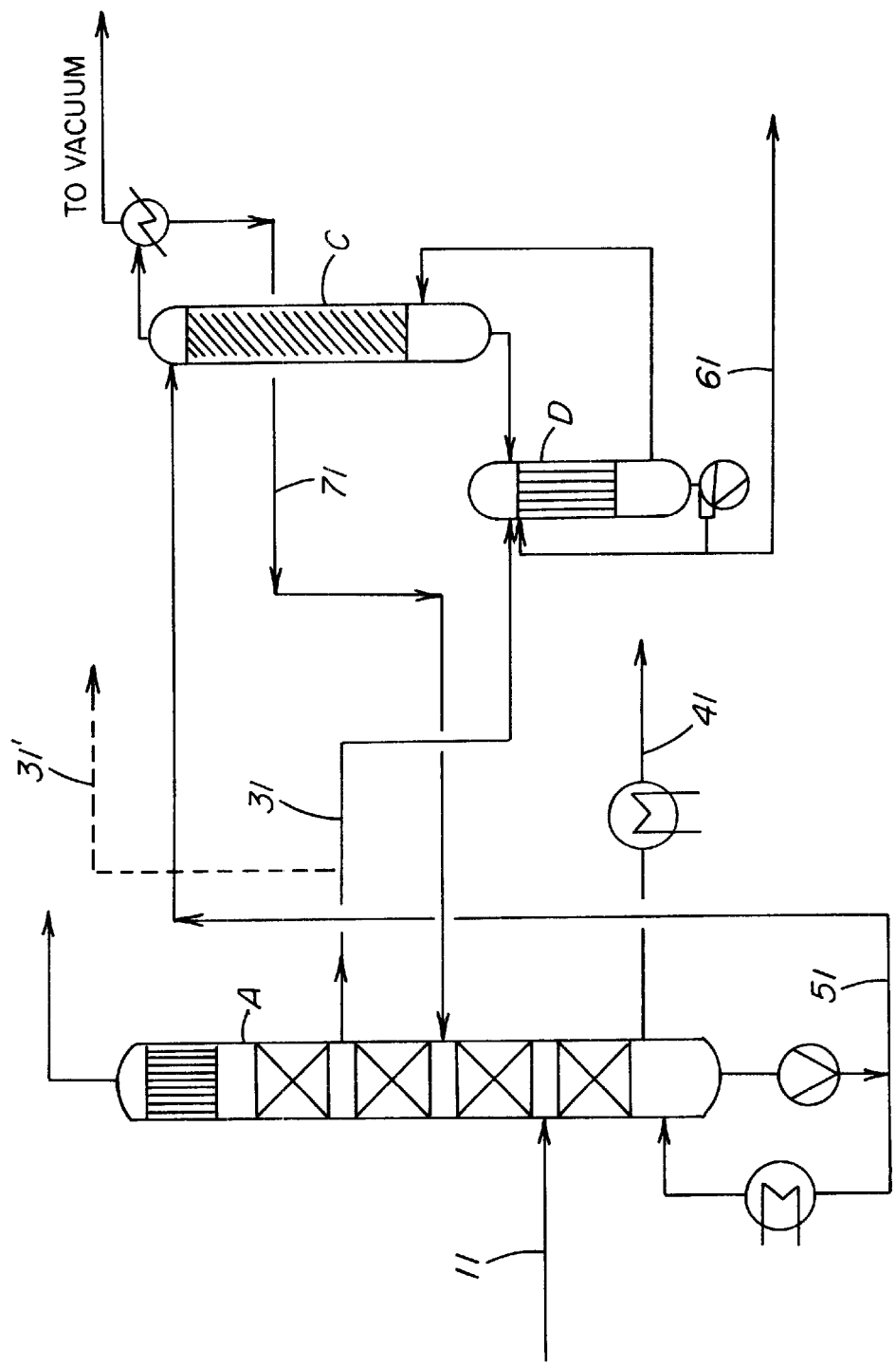
FIG. 3 illustrates an apparatus suitable for carrying out the separation of a mixture in accordance with a third embodiment of the process of the present invention. In this illustrated embodiment, the starting mixture is separated into three fractions in a single separation column.
Figure 4:
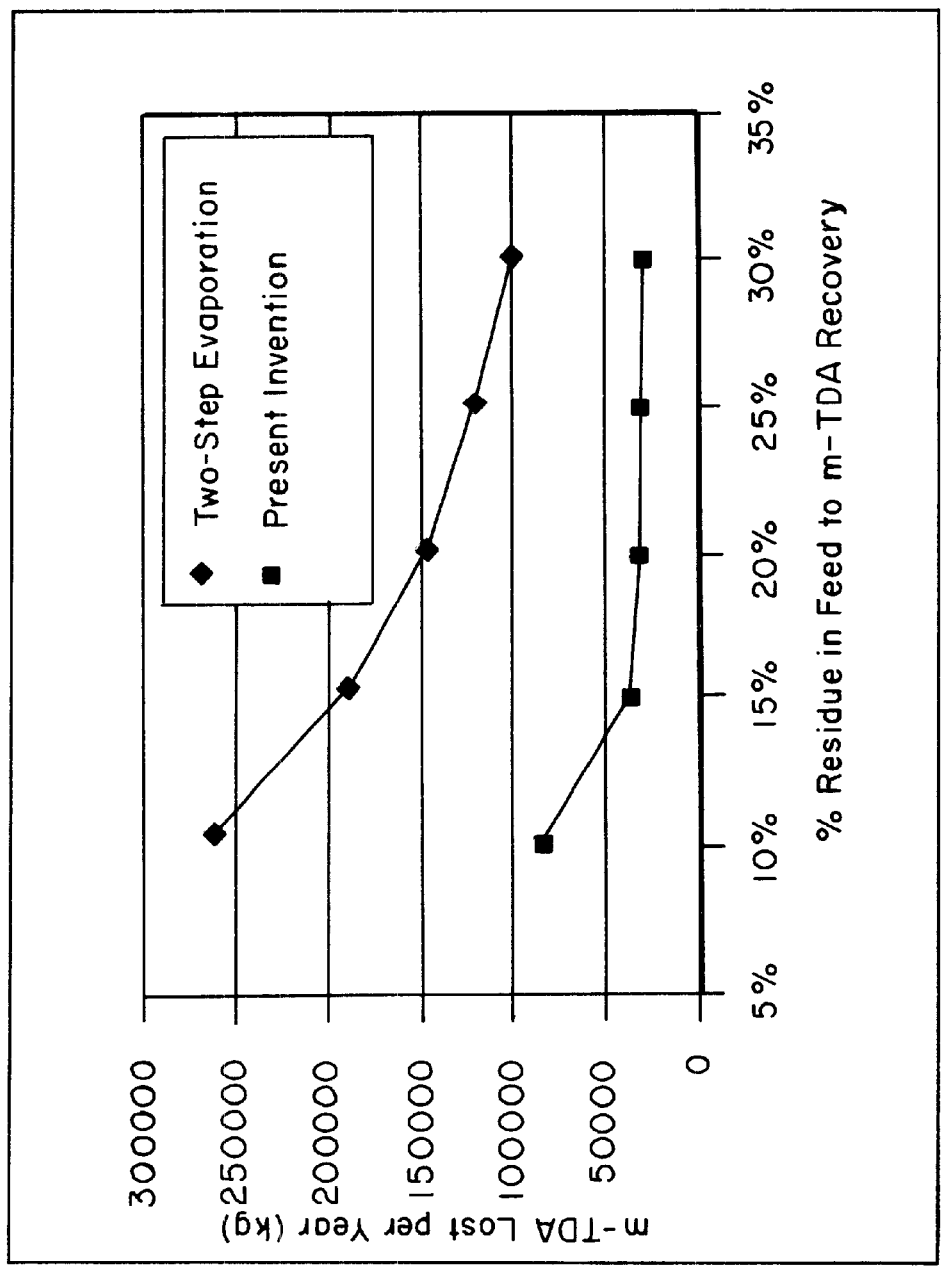
FIG. 4 is a graphic illustration of the amount of m-TDA lost at given residue concentration levels when the residue is treated by (1) the prior art two-step evaporation method of the type disclosed, for example, in U.S. Pat. No. 5,728,880 and (2) the process of the present invention.

In the apparatus shown in FIG. 3, the starting mixture, stream 11 is fed to separation column A. Stream 11 is separated in column A into streams 31, 41 and 51. Stream 31 which is composed substantially of ortho-TDA is recovered as the top product from column A. At least a portion of stream 31 is fed to evaporator D of stripping column C. Any portion of stream 31 which is not fed to evaporator D may be recovered. Any recovered portion of stream 31 is represented by a dotted line in FIG. 3.

Stream 41, the gas phase product recovered slightly above the bottom or from above one of the lowermost trays of column A, is substantially meta-TDA, the desired product.

Stream 51 which is recovered as the bottoms product from column A is composed substantially of meta-TDA and high boiling materials. Stream 51 is fed to stripping column C in which it is separated into stream 71 (the top product) and stream 61 (the bottom product). Stream 71 is fed back to separation column A.

In the embodiment of the present invention illustrated in FIG. 1, the starting mixture is separated into a low boiling fraction and a sump. The desired meta-TDA is subsequently recovered from the sump. In the embodiment of the present invention illustrated in FIG. 2, the starting mixture is separated into a sump product composed of unwanted by-products and an isomeric mixture composed of the ortho-TDA and meta-TDA isomers. It is the isomeric mixture of TDA which is subsequently separated. In the embodiment of the present invention illustrated in FIG. 3, the starting mixture is simultaneously separated into a high boiling, an intermediate boiling and a low boiling fraction. The sequence in which various fractions are separated from the starting mixture in accordance with the present invention may be varied without adverse effect.

In the process of the present invention, at least 97% by weight, preferably up to 99.8% of the m-TDA present in the original mixture is recovered. This degree of recovery is significantly better than that achieved by prior art processes such as the process disclosed in U.S. Pat. No. 5,728,880. The difference in the amount of m-TDA recovered by the process of the present invention and by prior art processes such as that disclosed in U.S. Pat. No. 5,728,880 is graphically illustrated in FIG. 4 in which the results shown for the process of the present invention were obtained using a 5 stage stripper apparatus. A 2.4% m-TDA content in the final residue was obtained by the process of the present invention when the ratio of o-TDA to m-TDA in the combined streams fed to the stripping column C and evaporator D was approximately 2:1. In contrast, an ortho-TDA to meta-TDA ratio of 6.5 in the "starting" residue/o-TDA mixture would be necessary to achieve this same level of meta-TDA in the residue generated by the two-stage evaporation process of U.S. Pat. No. 5,728,880.

The distillate recovered from the stripping column in the process of the present invention may be recycled directly to the first distillation stage of the process of the present invention. However, it may be advantageous to add sufficient o-TDA to that distillate to raise the o-TDA concentration to a concentration of from about 55 to about 98% by weight, based on total weight of the distillate, preferably from about 78 to about 96% by weight. Recycling of the distillate from the stripping column is advantageous in that the amount of heat necessary to achieve the distillation of the low-boiling fraction is reduced.

The process of the present invention has been found to be particularly advantageous for recovering m-TDA from starting residues in which the m-TDA content is at least 10%. For residues having an m-TDA content below 10%, the loss of m-TDA in the stripper system increases rapidly and eventually becomes restrictive. The process of the present invention may therefore be used to treat residues having an m-TDA content of less than 10% but the degree of recovery of m-TDA is not as high as that for residues having m-TDA contents greater than 10%.

Having thus described our invention, the following Examples are given as being illustrative thereof. All parts and percentages given in these Examples are parts by weight and percentages by weight, unless otherwise indicated.

EXAMPLES

Example 1

The apparatus shown in FIG. 1 was used to treat a TDA mixture generated by hydrogenating dinitrotoluene on a semi-continuous basis. A stripper column having the number of theoretical stages indicated within the parentheses next to the Table number was used to treat each of 4 different residues in which the ratio of o-TDA to m-TDA plus residue was as indicated in Tables. The composition of each of streams 1, 2, 3, 4, 5, 6 and 7 is indicated in the following Tables 1, 2, 3 and 4.

In Table 1–4, "HH-TDA" is used to identify methylcyclohexyldiamine and "HH-Toluidine" is used to identify methylcyclohexylamine.

TABLE 1

(Ten Stages, 70% Efficiency)

| Stream | 1 | 2 | 3 | 4 | 5 | 6 | 7 |
|---|---|---|---|---|---|---|---|
| Component | | | | | | | |
| 2,4-TDA Kg/h | 759.5 | 782.6 | 0.7 | 830.5 | 23.2 | 0.1 | 23.7 |
| 2,6-TDA Kg/h | 184.0 | 189.0 | 0.6 | 199.9 | 5.2 | 0.1 | 5.7 |
| 2,3-TDA Kg/h | 12.8 | 0.2 | 94.8 | 0.2 | 0.0 | 8.9 | 85.9 |
| 3,4-TDA Kg/h | 22.0 | 0.8 | 168.2 | 0.8 | 0.0 | 16.7 | 151.5 |
| 2,5-TDA Kg/h | 5.5 | 5.7 | 0.1 | 6.0 | 0.1 | 0.0 | 0.3 |
| Toluidine Kg/h | 0.3 | 0.0 | 0.0 | 0.0 | 0.0 | 0.0 | 0.0 |
| HH-Toluidine Kg/h | 0.0 | 0.0 | 0.0 | 0.0 | 0.0 | 0.0 | 0.0 |
| HH-TDA Kg/h | 3.7 | 0.0 | 0.2 | 0.0 | 0.0 | 0.0 | 0.2 |
| Residue Kg/h | 12.2 | 12.2 | 0.0 | 0.3 | 12.2 | 12.2 | 0.0 |
| Total Kg/h | 1000.0 | 990.5 | 264.7 | 1037.7 | 40.7 | 38.0 | 267.3 |
| Temp. (° C.) | 215.6 | 207.3 | 182.1 | 207.7 | 207.7 | 209.6 | 170.0 |
| Pressure (mbar) | | | | 90 | | | |
| Ratio o-TDA: m-TDA + Residue | | | | 6.5 | | | |

TABLE 2

(Ten Theoretical Stages)

| Stream | 1 | 2 | 3 | 4 | 5 | 6 | 7 |
|---|---|---|---|---|---|---|---|
| Component | | | | | | | |
| 2,4-TDA Kg/h | 759.5 | 769.5 | 0.8 | 809.5 | 10.1 | 0.1 | 10.8 |
| 2,6-TDA Kg/h | 184.0 | 186.1 | 0.8 | 195.2 | 2.2 | 0.1 | 3.0 |
| 2,3-TDA Kg/h | 12.8 | 0.2 | 113.3 | 0.2 | 0.0 | 4.2 | 109.5 |
| 3,5-TDA Kg/h | 22.0 | 0.8 | 205.5 | 0.8 | 0.0 | 7.9 | 197.5 |
| 2,5-TDA Kg/h | 5.5 | 5.6 | 0.2 | 5.8 | 0.1 | 0.0 | 0.2 |
| Toluidine Kg/h | 0.3 | 0.0 | 0.0 | 0.0 | 0.0 | 0.0 | 0.0 |
| HH-Toluidine Kg/h | 0.0 | 0.0 | 0.0 | 0.0 | 0.0 | 0.0 | 0.0 |
| HH-TDA Kg/h | 3.7 | 0.0 | 0.2 | 0.0 | 0.0 | 0.0 | 0.2 |
| Residue Kg/h | 12.2 | 12.3 | 0.0 | 0.6 | 12.3 | 12.2 | 0.2 |
| Total Kg/h | 1000.0 | 974.5 | 320.8 | 1012.2 | 24.7 | 24.3 | 321.0 |
| Temp. (° C.) | 215.6 | 207.3 | 182.1 | 214.5 | 214.5 | 216.3 | 170.0 |
| Pressure (mbar) | | | | 90 | | | |
| Ratio o-TDA: m-TDA + Residue | | | | 13 | | | |

TABLE 3

(Twenty Theoretical Stages)

| Stream | 1 | 2 | 3 | 4 | 5 | 6 | 7 |
|---|---|---|---|---|---|---|---|
| Component | | | | | | | |
| 2,4-TDA Kg/h | 759.5 | 763.7 | 0.1 | 774.0 | 4.3 | 0.0 | 4.3 |
| 2,6-TDA Kg/h | 184.0 | 184.8 | 0.1 | 187.2 | 0.9 | 0.0 | 1.0 |
| 2,3-TDA Kg/h | 12.8 | 0.2 | 12.2 | 0.2 | 0.0 | 1.8 | 10.4 |
| 3,4-TDA Kg/h | 22.0 | 0.7 | 22.4 | 0.8 | 0.0 | 3.4 | 18.9 |
| 2,5-TDA Kg/h | 5.5 | 5.5 | 0.0 | 5.6 | 0.0 | 0.0 | 0.0 |
| Toluidine Kg/h | 0.3 | 0.0 | 0.0 | 0.0 | 0.0 | 0.0 | 0.0 |
| HH-Toluidine Kg/h | 0.0 | 0.0 | 0.0 | 0.0 | 0.0 | 0.0 | 0.0 |
| HH-TDA Kg/h | 3.7 | 0.0 | 0.0 | 0.0 | 0.0 | 0.0 | 0.0 |
| Residue Kg/h | 12.2 | 12.2 | 0.0 | 1.1 | 12.2 | 12.2 | 0.0 |
| Total Kg/h | 1000.0 | 967.2 | 34.8 | 968.9 | 17.4 | 17.4 | 34.7 |
| Temp. (° C.) | 215.6 | 207.3 | 182.1 | 226.7 | 226.7 | 229.5 | 170.0 |
| Pressure (mbar) | | | | 90.0 | | | |
| Ratio o-TDA: m-TDA + Residue | | | | 2 | | | |

TABLE 4

(Five Stages, 70% Efficiency)

| Stream | 1 | 2 | 3 | 4 | 5 | 6 | 7 |
|---|---|---|---|---|---|---|---|
| Component | | | | | | | |
| 2,4-TDA Kg/h | 759.5 | 774.6 | 1.9 | 821.1 | 15.2 | 0.1 | 16.9 |
| 2,6-TDA Kg/h | 184.0 | 187.3 | 1.3 | 197.8 | 3.4 | 0.1 | 4.6 |
| 2,3-TDA Kg/h | 12.8 | 0.2 | 221.0 | 0.2 | 0.0 | 6.3 | 214.7 |
| 3,4-TDA Kg/h | 22.0 | 0.8 | 396.6 | 0.8 | 0.0 | 11.8 | 384.8 |
| 2,5-TDA Kg/h | 5.5 | 5.6 | 0.2 | 5.9 | 0.1 | 0.0 | 0.3 |
| Toluidine Kg/h | 0.3 | 0.0 | 0.0 | 0.0 | 0.0 | 0.0 | 0.0 |
| HH-Toluidine Kg/h | 0.0 | 0.0 | 0.0 | 0.0 | 0.0 | 0.0 | 0.0 |
| HH-TDA Kg/h | 3.7 | 0.0 | 0.4 | 0.0 | 0.0 | 0.0 | 0.4 |
| Residue Kg/h | 12.2 | 12.4 | 0.0 | 0.5 | 12.4 | 12.2 | 0.3 |
| Total Kg/h | 1000.0 | 980.9 | 621.4 | 1026.3 | 31.1 | 30.4 | 621.9 |
| Temp. (° C.) | 215.6 | 207.3 | 182.1 | 210.6 | 210.6 | 212.2 | 170.0 |
| Pressure (mbar) | | | | 90.0 | | | |
| Ratio o-TDA: m-TDA + Residue | | | | 20 | | | |

Although the invention has been described in detail in the foregoing for the purpose of illustration, it is to be understood that such detail is solely for that purpose and that variations can be made therein by those skilled in the art without departing from the spirit and scope of the invention, except as it may be limited by the claims.

What is claimed is:

1. A process for separating a mixture of materials having different boiling points comprising
   a) distilling the mixture to separate it into
      (1) a low boiling fraction,
      (2) an intermediate fraction having a boiling point between that of the low boiling fraction (1) and a high boiling fraction, and
      (3) a high boiling fraction,
   b) feeding the high boiling fraction to a stripping column,
   c) stripping the high boiling fraction in the stripping column with the vapors of a portion of the low boiling fraction,
   d) recovering a mixture composed of a portion of the low boiling fraction and a portion of the high boiling fraction in which substantially no intermediate fraction is present as a bottoms product from the stripping column,
   e) recovering a mixture composed of a portion of the low boiling fraction and a portion of the intermediate fraction as a distillate from the stripping column, and f) recycling the mixture recovered in step e) to step a).

2. The process of claim 1 in which the mixture of materials having different boiling points is an isomeric mixture of toluene diamine.

3. The process of claim 2 in which at least 10% m-TDA is present in the isomeric mixture.

4. The process of claim 1 in which the stripping column used in step b) has at least 5 stages.

5. The process of claim 1 in which the relative vapor pressure of the intermediate fraction to the high boiling fraction is at least 3:1 and the relative vapor pressure of the low boiling fraction to the intermediate fraction is no greater than 30:1.

6. The process of claim 1 in which the relative vapor pressure of the intermediate fraction to the high boiling fraction is at least 25:1 and the relative vapor pressure of the low boiling fraction to the intermediate fraction is no greater than 5:1.

7. An apparatus suitable for separating a mixture of materials having different boiling points in accordance with the process of claim 1 comprising:

a) at least one separation column capable of separating the mixture into a high boiling fraction, an intermediate boiling fraction and a low boiling fraction and b) a stripping column in which the fraction separated in the separation column which contains the desired product is stripped with at least a portion of the low boiling fraction.

8. The apparatus of claim 7 in which the stripping column has at least 5 stages.

9. The apparatus of claim 7 in which the stripping column has from 5 to 30 stages.

* * * * *